United States Patent
Andrews et al.

(10) Patent No.: US 6,383,526 B1
(45) Date of Patent: May 7, 2002

(54) PROCESS FOR THE EXTRACTION OF VALERIAN ROOT

(75) Inventors: Michael J. Andrews; Amaresh Basu, both of San Diego, CA (US)

(73) Assignee: Ancile Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/620,801

(22) Filed: Jul. 21, 2000

Related U.S. Application Data

(63) Continuation-in-part of application No. 09/358,375, filed on Jul. 21, 1999.

(51) Int. Cl.$^7$ ............................................... A61K 35/78
(52) U.S. Cl. ...................................... 424/733; 424/773
(58) Field of Search ................................. 424/773, 733

(56) References Cited

U.S. PATENT DOCUMENTS

| | | |
|---|---|---|
| 3,420,935 A | 1/1969 | Majnarich |
| 3,422,090 A | 1/1969 | Thies et al. |
| 3,869,476 A | 3/1975 | Thies et al. |
| 4,263,285 A | 4/1981 | Debate et al. |
| 4,313,930 A | 2/1982 | Wischniewski et al. |
| 4,382,961 A | 5/1983 | Nedeczky et al. |
| 4,946,682 A | 8/1990 | Stirnadel et al. |
| 4,981,688 A | 1/1991 | Ayroles et al. |
| 5,211,948 A | 5/1993 | Cerise et al. |
| 5,322,688 A | 6/1994 | Schwabe |
| 5,714,150 A | 2/1998 | Nachman |

FOREIGN PATENT DOCUMENTS

| | | |
|---|---|---|
| CH | 0631624 A | 8/1982 |
| DE | 03112737 A1 | 10/1982 |
| GB | WO 09/13054 A1 | 4/1998 |

OTHER PUBLICATIONS

K.O. Hiller et al.: Neuropharmacological Studies on Ethanol Extracts of *Valeriana Officinalis* L.: Behavioural and Anti-convulsant Propertyies Phytotherapy Research., 10:2 145–151 (1996).

Deutsches Arzneibuch DAB 7 listing for "*Tinctura Valerianae*" copy, reproduction and translation. German Pharm. 7th Ed—(1967).

Chemical Abstracts; Pharmaceutical Chemistry 26:3873 (1932)—Abstract of Traberg, J.E., *Dansk. Tids. Farm.* 6:17–19 (1932).

Botaniclas International Online Catalog, http://www.botanicalsintl.com/ Obtained Aug. 29, 2001.

Nutrition Science New, Sep. 1998; "Standardizing Extracts: S. Dental;Boon or Bane"; "Keep Natural products Natural," C. Cabrera "USP Finds Valerian Evidence Lacking", http//www.usp.org/ Obtained Nov. 7, 2000.

Gardening, "Welcome to the herbhouse," http//pages.prodigy.com/gardenshop Obtained Aug. 29, 2000.

Box, R. et al., Phytochem, Anal., vol. 7 143–151 (1996).

Canyon Herbs and Acupuncture, "Making an Herbal Extract," Jul. 9, 2000.

*Primary Examiner*—Herbert J. Lilling
(74) *Attorney, Agent, or Firm*—Knobbe, Martens, Olson & Bear, LLP

(57) ABSTRACT

A process for preparing a pharmaceutically-active extract of the root of a plant of the family Valerianacae, specifically, *Valeriana officinalis* L., is described. This process comprises the steps of adding the roots to an alcoholic extraction solvent to form a mixture, wherein the alcoholic extraction solvent comprises between approximately 50% to approximately 100% (v/v) in a remainder of water, and heating the mixture to a temperature of between approximately 70° C. to approximately 80° C. for a period of at least approximately two hours. By this process valerenic acid is obtained in the extract, and the extract has a content of valepotriates and valepotriate degradation products or derivatives that is substantially reduced with respect to the content of valepotriates in the roots, and has a content of valerenic acids that is not substantially reduced with respect to the content of valerenic acids in the roots. Also preferably, the content of volatile oils in the extract is also not substantially with respect to the content of volatile oils in the roots. A pharmaceutically-active extract of the root of a plant of the family Valerianaceae is also described. This extract is obtained by a process comprising the steps of adding the roots to an alcoholic extraction solvent to form a mixture, wherein the alcoholic extraction solvent comprises between approximately 50% (v/v) to approximately 100% (v/v) in a remainder of water, and heating the mixture to a temperature of between approximately 70° C. to approximately 80° C. for a period of at least approximately two hours. This extract may be used in the formulation of an ingestible form, preferably exhibiting sedative and/or muscle relaxant, and/or anxiolytic activity.

42 Claims, No Drawings

PROCESS FOR THE EXTRACTION OF VALERIAN ROOT

PRIORITY CLAIM

This application claims priority from and is a continuation-in-part of U.S. patent application Ser. No. 09/358,375, PROCESS FOR THE EXTRACTION OF VALERIAN ROOT, filed Jul. 21, 1999, by Andrews et al., the entire disclosure of which is incorporated by reference herein.

BACKGROUND OF THE INVENTION

1. Field of the Invention

The present invention relates to a process for isolating a pharmaceutically-active extract from a plant root, and more generally, to a novel method for preparing a medicament containing this extract. More specifically, the present invention relates to a process for maximizing the yield of valerenic acid and other valerenic acids and their derivatives, while simultaneously minimizing the yield of valepotriates and valepotriates decomposition products or derivatives in an extract of the root of the plant *Valeriana officinalis* L.

2. Description of the Related Art

Extracts of the root of the plant *Valeriana officinalis* L. (*V. officinalis* L.) have been used for medicinal purposes for over a century. Certain valerian extracts, including aqueous extracts, are known to have sedative and anxiolytic effects, but the active components have not been clearly and positively identified. [Leathwood P. D., Chauffard F., Heck E., and Munoz-Box R. Aqueous extract of valerian root (*Valeriana officinalis* L.) improves sleep quality in man. Pharmacology, Biochemistry and Behavior, 17:65–71, 1982; Leathwood P. D. and Chauffard F. Aqueous extract of valerian reduces latency to fall asleep in man. Planta Medica, 2:144–148 (1985)] Such effects are described by Balandrin et al. in U.S. Pat. No. 5,506,268, which is incorporated by reference herein in its entirety. Presently, valerian extracts are available as dietary supplements; these dietary supplements primarily comprise dried root or extracts from the root, formula into tablets or soft gelatin capsules. Each dose contains between approximately 50 mg and approximately 1 gram of dried root or extract. The use of these dietary supplements is extensive, with an estimated 210 million doses sold annually in the United States and 125 million doses sold annually in Europe. See Grunwald, J., "The European Phytomedicines Market—Figures, Trends Analyses" Herbal Gram, 1995.

*V. officinalis* L. is a member of the Valerianaceae family. This plant grows from a short rhizome to approximately 2 meters in height, it flowers, and then dies back again in the winter. *Valeriana officinalis* L. has pinnately-divided leaves, typically with six to ten pairs of lance-shaped leaflets, and bears many small white or pink flowers in a dense head of several stalked clusters. These heads bare small (5 millimeters) tapered seeds.

It is not fully understood which constituents of *Valeriana officinalis* L., and/or of the other heretofore unidentified members of the Valerianaceae family, are responsible for the sedative and/or anxiolytic action of valerian extracts. Nonetheless, the valepotriates (iridoids) as well as valerenic acid, a sesquiterpenoid compound, and the derivatives of valerenic acid (for example, acetoxyvalerenic acid and hydroxyvalerenic acid) along with the kessane derivatives, valeranone, valerenal, and certain amino acids are present in valerian extracts. Of these components, the valepotriates and valerenic acids are generally considered to contribute to the sedative action of valerian extracts, but have not been clearly and positively identified as such. See Hendriks H. et al. "Pharmacological Screening of valerenal and some other components of essential oil of *Valeriana officinalis*" Planta Medica 42, 62–68 (1981); Bos R. et al., "Analytical aspects of phytotherapeutic valerian." (1996); Houghton P. J., Valerian. The Genus Valeriana. Harwood Academic Publishers, London (1997).

Valepotriates (iridoids) are triesters of polyalcohols with an iridoid structure. They are unstable, thermolabile compounds that decompose in alcoholic solutions and under acidic or alkaline conditions. See Bos R. et al. Analytical aspects of Phytotherapeutic Valerian preparation, 1996; 7:143–151. The major decomposition products of diene type valepotriates are baldrinals, including: baldrinal (from the valepotriates valtrate and acevaltrate) and homobaldrinal (from the valepotriate isovaltrate). Relative to the above-described valepotriates, valerenic acid and its derivatives (for example, acetoxyvalerenic acid and hydroxyvalerenic acid) are chemically stable. While valepotriates and valepotriate decomposition products or derivatives are found in many species of Valerianaceae, *Valeriana officinalis* L. is the only species that has been identified as possessing extractable valerenic acid in its roots. The structures of valerenic acids and certain valepotriates and valepotriate decomposition products are presented below.

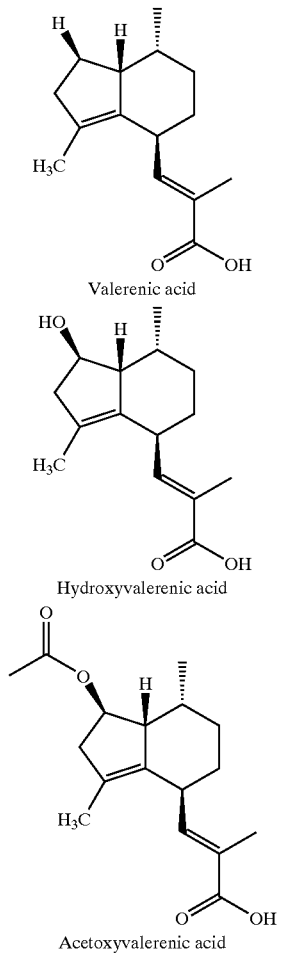

Valerenic acid

Hydroxyvalerenic acid

Acetoxyvalerenic acid

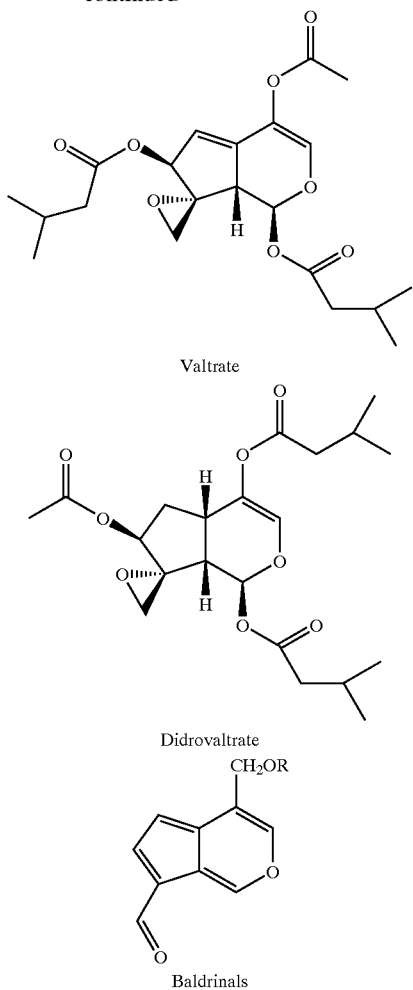

Valtrate

Didrovaltrate

Baldrinals

Several processes are known for the extraction of valerian roots, but none of these known processes simultaneously retains valerenic acid, maximizes the content of the valerenic acids (e.g., of valerenic acid and of the valerenic acid derivatives), and minimizes the content of valepotriates. Indeed, certain of these extraction processes were designed to retain or maximize the yield of valepotriates. For example, Broese et al., CH 000046778 (1978), describe obtaining a stable extract of a valerian preparation in which the essential valepotriates are present undiminished in the resultant extract, and Wischniewski et al., U.S. Pat. No. 4,313,930 (1982), describe the production of a stable valepotriate composition, through the use a pharmaceutically acceptable sheathing material, from a pharmaceutically active Valerianacea extract. Other known extraction processes focus on removing the odors associated with the valepotriate and valepotriate derivatives, but do not maximize the content of valerenic acid and the valerenic acid derivatives.

For example, Cerise et al., U.S. Pat. No. 5,211,948 (1993), describe extracting Valerian roots with water over a period of 2 to 5 hours at a temperature from 65 to 75° C. This water-based extraction is described as leading "to degradation of the valepotriates while preserving the valerenic acids of the valerian roots." The '948 patent also states that extraction of valerian roots with hot water (2 to 5 hrs at 65–75° C.), preferably three successive times, leads to degradation of the valepotriates while "preserving" the valerenic acids. However, the results of the current examples, see esp. Examples 6–10, indicate that the valerenic acids are "preserved" in the roots and are not extracted.

Valerenic acid is a chemically stable compound that is used as an identification test for *V. officinalis* in the United States Pharmacopoeia (USP23-NF18, Supplement 8). Thus, to develop a valerian based sedative product, it would be beneficial to enrich valerenic acids in the extract or substantially retain valerenic acid from the root. Due to poor solubility of valerenic acids in water, the process of the '948 Patent is inefficient in extracting these compounds. The extraction process of the present invention, on the other hand, efficiently enriches valerenic acids. In this respect, the present invention is far more superior than the Cerise process.

Other extraction processes are known, but are conducted in the presence of unusual, expensive, or otherwise undesirable solvents and/or at unusual or undesirable conditions, such as low pH. For example, Thies et al., U.S. Pat. No. 3,422,090 (1969) describe extracting roots and rhizomes of plants of the genus Valeriana at a temperature below 30° C. with a lipophilic solvent in the presence of an aliphatic carboxylic acid, specifically glacial acidic acid, within a pH range of about 3 to about 7. Gehrlicher, DE 03112737 (Mar. 31, 1981) ("the '737 application") describes obtaining epoxide-free sedative agents from plants of the Valerianaceae family by extracting at elevated temperatures in the presence of weak acids and catalytic amounts of strong acids at pH<3, with either lower aliphatic alcohols or mixtures of lower aliphatic alcohols with water or anhydrous non-polar solvents. The process of the '737 application, however, retains baldrinals and other valepotriate decomposition products in the extract.

SUMMARY OF THE INVENTION

A process for preparing a pharmaceutically-active extract of the root of a plant of the family Valerianacae, specifically, *Valeriana officinalis* L., is described. This process comprises the steps of adding the roots to an alcoholic extraction solvent to form a mixture, wherein the alcoholic extraction solvent comprises between approximately 50% to approximately 100% (v/v) ethanol in a remainder of water, and heating the mixture to a temperature of between approximately 70° C. to approximately 80° C. for a period of at least two hours. By this process the extract contains valerenic acids and has a content of valepotriates and valepotriate degradation products that is substantially reduced with respect to the content of valepotriates in the roots, and may have a content of valerenic acids that is not substantially reduced with respect to the content of valerenic acids in the roots, and also may have a content of volatile oils that is not substantially reduced with respect to the content of volatile oils in the roots. The process may be performed at pH greater than about 3.0, greater than about 5.0, or greater than about 7.0.

A pharmaceutically-active extract of the roots of a plant of the family Valerianaceae is also described. This extract is obtained by a process comprising the steps of adding the roots to an alcoholic extraction solvent to form a mixture, wherein the alcoholic extraction solvent comprises between approximately 50% (v/v) to approximately 100% (v/v) ethanol in a remainder of water, and heating the mixture to a temperature of between approximately 70° C. to approximately 80° C. for a period of at least two hours. This extract may then be used in a pharmaceutically active formulation preferably exhibiting sedative and/or muscle relaxant, and/or anxiolytic activity.

DETAILED DESCRIPTION OF THE PREFERRED EMBODIMENTS

One objective of the present invention is to provide a process by which valerenic acid and its derivatives (e.g., acetoxyvalerenic acid and hydroxyvalerenic acid) are isolated in an extract of the roots of plants of the Valerianaceae family. More specifically, plants of the species *Valeriana officinalis* L. are used. Another, objective of the present invention is to provide a process by which valepotriates (iridoids) are substantially reduced in an extract with respect to their content in the roots, and preferably are not purified and/or isolated in an extract of the above-described roots. Another objective of the present invention is to provide a relatively inexpensive process that can be performed at commercial scale for the production of an extract having valerenic acids specifically, and valerenic acid and its derivatives (for example, acetoxyvalerenic acid and hydroxyvalerenic acid) generally, from the above-described roots. Another object of the present invention is to provide an extract process through which the extracted roots may be chemically identified as the roots of *Valeriana officinalis* L. Yet another object of the present invention is to provide a process for preparing a medicament containing an extract of the above-described roots. In the preferred embodiment of the extraction process of the present invention, but not necessarily in all embodiments of the extraction process of the present invention, these objectives are simultaneously met. Most preferably, the extract process of the present invention significantly reduces the amount of valepotriates in the extract and the amount of valerenic acid and/or valerenic acids is unaltered in the extract when compared to known processes.

According to the present invention, at least one of these objectives is met, at least in part, through an extraction process. In conjunction with this extraction process, methods for processing the root prior to extraction, for forming a drug substance via the addition of excipient, for drying and milling the drug substance, and for formulating an ingestible entity, such as a tablet, capsule, tea, suspension, or other medicinal food, are described. These methods provide a medicament of the present invention, which contains the extract of the present invention.

Shown below are structures of exemplary compounds isolated according to the preferred methods described herein.

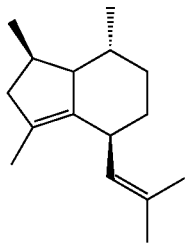

wherein, for the following compounds, R and R' are defined as follows:

|  | R | R' |
| --- | --- | --- |
| Valerenic Acid | H | $CO_2H$ |
| Hydroxyvalerenic Acid | OH | $CO_2H$ |
| Acetoxyvalerenic Acid | $OCOCH_3$ | $CO_2H$ |
| Valerenal | H | CHO |
| Valerenol | H | $CH_2OH$ |

Extracts of *V. officinalis* L. roots exhibit sedative and anxiolytic action. Pharmacology studies indicate that *V. officinalis* exerts sedative properties apparently by a combination of central nervous system (CNS) depression and smooth muscle relaxation. *V. officinalis* has been shown to decrease mobility, potentiate barbiturate induced sleep time, alter performance on rotorod and traction tests, act as an anti-convulsant and exert anti-spasmolytic properties. Studies in animals (mainly rodents) show that individual constituents of *V. officinalis* exert similar sedative and pharmacological properties, although they are unable to account for the total activity of the plant See Houghton P. J., Valerian. The Genus Valeriana. Harwood Academic Publishers, London (1997).

Studies intended to attribute the activity of plant extracts to individual constituents typically take into account the amount of one or more active compound(s) present in the plant extract and the concentration which shows activity in a test system. HPLC analysis of the extract obtained from the current process shows that the extract may contain approximately 0.0—to approximately 0.50% and preferably 0.30% valerenic acid, approximately 0.0 to approximately 0.50% and preferably 0.37% acetoxyvalerenic acid, and approximately 0.0 to approximately 0.1% and preferably 0.01% hydroxyvalerenic acid. Analysis of the extract by steam distillation shows that the extract may contain approximately 0.0 to approximately 5% of total volatile oils and preferably 1%, 2%, 3%, or 4% of total volatile oils.

Valerenic Acids

Valerenic acids are components of *V. officinalis* extracts, and of extracts of other members of the family Valerianaceae, that are likely responsible for the sedative activity of valerian. The valerenic acids (for example, valerenic acid, acetoxyvalerenic acid and hydroxyvalerenic acid) of *V. officinalis* may exert sedative properties. For example, valerenic acid administered intraperitoneally (IP) at a dose of 100 mg/kg, caused a decrease in motor activity, a decrease in respiratory rate, absence of righting reflex, ataxia, a decrease of abdominal muscle tone and a decrease in rotarod performance in mice. See Hendrick H, Bos R, Allersma D, Malingre T, and Koster A. Pharmacological Screening of Valerenal and some other Components of Essential Oil of *Valeriana officinalis*. Planta Medica: 1981; 42: 62–68. In a follow up study, the same researchers showed that valerenic acid influenced performance on both the rotarod and traction tests with statistical significance obtained at 100 mg/kg, IP. Valerenic acid was also shown to potentiate pentobarbital induced sleeping time at doses of 50 and 100 mg/kg, IP. See Hendricks H, Bos R, Woerdenbag H and Koster A, Central Nervous Depressant Activity of Valerenic Acid in the Mouse. Planta Medica: 1985; 51: 28–31. The anti-convulsant properties of valerenic acid have been characterized, see Hiller K. and Zetler G. "Neuropharmacological studies on ethanol extracts of *Valeriana officinalis* L.: Behavioral and anticonvulsant properties" *Phytotherapy Res.* 10 (1996) 145–151; it was shown that valerenic acid antagonized picrotoxin induced convulsions at 12.5 and 25 mg/kg, IP in mice. At a concentration of 1 mmole/liter, valerenic acid and acetoxyvalerenic acid were shown to inhibit the enzyme system which catalyses breakdown of GABA in the brain by 20% and 38%, respectively. See Riedel E, Hansel R and Ehrke G. Inhibition of GABA catabolism by valerenic acid derivatives. Planta Medica: 1982 ; 46: 219–220. An increase in brain concentrations of GABA, a potent central nervous system (CNS) depressant, may thus lead to a decrease in CNS activity and sedation.

One aspect of the current method is useful in verifying that the particular roots to be extracted are roots of the species V. officinalis L. and not of another plant, or more specifically of another member of the Valerianaceae family. And because many of the plants in this family are phenotypically similar and are therefore capable of being substituted for one another, a preferable means to identify V. officinalis L. is to identify valerenic acid directly in the extract.

Preferred extraction processes according to the invention, unlike known methods of extracting V. officinalis L. roots from water, yields a measurable amount of valerenic acid. As shown herein, see esp. Examples 6, 7, 8, 9, and 10, the extraction of V. officinalis L. roots in water yields substantially less valerenic acids than the methods described herein. As noted above, the present extraction method is therefore preferable to, and provides benefits not obtainable through the use of known water-based extraction methods. For example, the present process allows for the extraction of a pharmaceutically-effective composition that can be independently verified as being from the roots of V. officinalis L., rather than from the roots of another plant or of a phenotypically-similar member of the Valerianaceae family.

In another embodiment of the invention, the amount of total valerenic acids or of a specific valerenic acid may be a marker for the strength/potency of the extract. For example, 0.6%–1.0% total valerenic acids may serve as such a marker.

Volatile Oils

Another preferred aspect of the extracts and extraction methods provided herein that is distinct from known valerian extractions and extraction methods concerns the yield of a measurable amount of volatile oil in the extract. As shown in, for example, Example 10, described in detail below, the extraction of V. officinalis L. roots in water does not yield isolatable volatile oil.

The volatile oils of V. officinalis are very complex mixture of mostly mono- and sesquiterpenoids. Over 150 compounds have been identified in the volatile oil fraction and have been described. See Bos R. Anaylytical and Phytochemical Studies on Valerian and Valerian Based Preparations. Thesis: Offsetdrukkerij Ridderprint B. V., Ridderkerk: 1997; 13–21 and 77–93.

Several studies have reported sedative effects of the total volatile oil and/or volatile oil constituents (kessoglycol diacetate, kessoglycol 2-acetate, kessylglycol 8-acetate, valerenal, and valerenone) in in vivo animal models of sedation. See Hazelhoff B, Malingre T and Meijer D. Antispasmodic effects of valeriana compounds: an in-vivo and in-vitro study on guinea-pig ileum. Arch Int Pharmacodyn Ther.: 1982; 257(2): 274–87; Hendricks, et al. 1981; Hikino H, Hikino Y, Kobinata H, Aizawa A, Konno C and Oh'Izumi Y. Sedative Principles of Valeriana Roots. Shoyakugaku Zasshi: 1980; 34(1): 19–24. Thus, the volatile oil may contribute to the overall sedative properties of the extract.

However, even the most abundant volatile oil is generally a minor component in the extract. Thus, individual components of the volatile oil-will not typically, but may, be justified as a useful marker for monitoring the consistency of the extract across manufactured batches.

In another embodiment of the invention, therefore, the amount of total volatile oils may be a marker for the strength/potency of the extract. For example, approximately 0.6% to approximately 2.2% total volatile oil may serve as such a marker.

The volatile oil content typically ranges from approximately 0% to approximately 5.0%, and preferably approximately 0.6 to approximately 2.2% (v/w).

In sum, the pharmacology studies cited in the literature indicate that volatile oil components of V. officinalis may be related to sedative activity. The current process may retain this component and the assay of the total volatile oil component, as the measurement from steam distillation indicates that the product has about 0.0% to about 5% of volatile oil. The current method thus may provide a way of control for the total amount of volatile oil within the extract. Accordingly, the present extraction method is preferable to, and provides benefits not obtainable through, the use of known water-based extraction methods.

Valepotriates and Valepotriate Decomposition Products

Another aspect of the current method that is distinct from known valerian extraction method concerns the in-process reduction of the content of valepotriates in the extracts. Valepotriates are triesters of polyalcohols with an iridoid structure and an epoxy group that have reported cytotoxic and mutagenic properties. Valepotriates are divided into two main groups: diene type (which include valtrate, isovaltrate, and acevaltrate) and monoene type (which include didrovaltrate and isovaleroxyhydroxydidrovaltrate (IVHD). Valepotriates are thermolabile and decompose under acidic, alkaline or alcoholic conditions. See Bos, 1996. Shown below are chemical structures of certain valepotriates.

Diene Valepotriates

|  | $R_1$ | $R_2$ | $R_3$ |
|---|---|---|---|
| Valtrate | $COCH_2CH(CH_3)_2$ | $COCH_2CH(CH_3)_2$ | $COCH_3$ |
| Isovaltrate | $COCH_2CH(CH_3)_2$ | $COCH_3$ | $COCH_2CH(CH_3)_2$ |
| Acevaltrate | $COCH_2C(CH_3)_2OCOCH_3$ | $COCH_2CH(CH_3)_2$ | $COCH_3$ |

-continued

Monoene Valepotriates

|   | R₁ | R₂ | R₃ | R₄ |
|---|---|---|---|---|
| Didrovaltrate | COCH$_2$CH(CH$_3$)$_2$ | COCH$_3$ | COCH$_2$CH(CH$_3$)$_2$ | H |
| IVHD | COCH(OCOCH$_2$CH(CH$_3$)$_2$)CH(CH$_3$)$_2$ | COCH$_2$CH(CH$_3$)$_2$ | COCH$_3$ | OH |

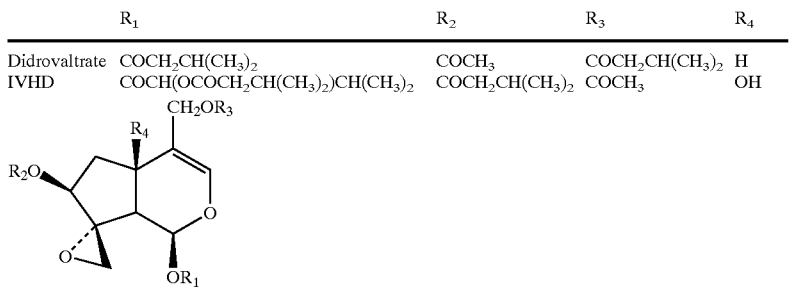

While valepotriates may contribute to the pharmaceutical activity of valerian extracts, valepotriates and their decomposition products are also potentially dangerous. For example, valepotriates have been shown to be cytotoxic in vitro, and exhibit potential mutagenic activity. See Von der Hude W., Scheutwinkel-Reich M., Braun R., and Dittmar W. "In vitro mutagenicity of valepotriates" *Arch Toxicol* 56 (1985) 267–71; Von der Hude W., Scheutwinkel-Reich M., and Braun R. "Bacterial mutagenicity of the tranquilizing constituents of Valerianaceae roots." *Mutat Res* 169 (1986) 23–7). Also, orally-administered valepotriates reach the brain and other organs in vivo, and have been shown to be capable of irreversibly alkylating DNA and proteins (Wagner, H. and Jurcic, K, Planta Med. (1980) 38:366–376). As cytotoxic and mutagenic effects have been reported for the valepotriates the present invention provides a method of control for the levels of this class of compounds. This process comprises adding the ground roots to an alcoholic extraction solvent and heating to a temperature between 70° C. and 80° C. for a period of at least three hours. By this process the extract contains valerenic acids but has levels of valepotriates that are substantially reduced compared to the content of valepotriates that occur naturally in the roots of the plant.

Valepotriates are not unique to the genus officinalis, but are known constituents of most Valeriana species. *V. officinalis* mainly contains valepotriates of the diene type (valtrate, isovaltrate, and some acevaltrate), whereas both *V. wallichii* and *V. edulis* also contain considerable amounts of the monoene type (didrovaltrate and isovaleroxyhydroxydidrovaltrate). See Houghton, 1997. A few studies explored the content of different valepotriates in *V. officinalis* root. The studies indicate that only the diene valepotriates, valtrate and isovaltrate, are present in significant amounts, and all other valepotriates are present in trace amounts (see Table 1, below).

TABLE 1

Content of Valepotriates in Dried *V. officinalis* Roots

| Valepotriate | Content in dried root (%) | Reference |
|---|---|---|
| Valtrate | 0.095–0.95 | Granicher et al., 1995; Sener et al., 1987 |
| Isovaltrate | 0.05–0.63 | Granicher et al., 1995; Hazelhoff et al., 1979; 1981; Sener et al., 1987 |
| Acevaltrate | 0.02 | Hazelhoff et al., 1979 Granicher et al., 1995; |
| Didrovaltrate | 0.01–0.02 | Sener et al., 1987 |
| IVHD | 0.055 | Granicher et al., 1995 |

The data presented in Example 11 confirms the above information.

In addition, according to a preferred aspect of the invention, a lower limit for total valepotriates in the extract may be set as a process condition. For example, valtrate and isovaltrate may be quantitatively monitored because they are present in significant quantities in the *V. officinalis* biomass. Total valepotriate levels in the extract produced by the current process should preferably be <0.1%. This ensures that the current extraction process consistently reduces valepotriates in the extract regardless of the starting concentration in the original biomass.

Major decomposition products of the valepotriates are the baldrinals, including baldrinal (from valtrate and acevaltrate) and homobaldrinal (from isovaltrate). See Bos, 1996; Houghton, 1997. As described in Bos (1997), the baldrinals are chemically reactive and may subsequently form polymers, although no evidence of polymerization was provided. Chemical structures of exemplary baldrinals are provided below.

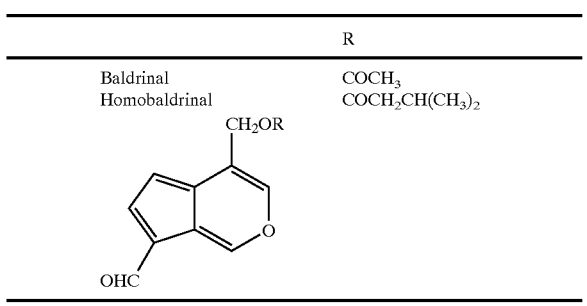

| | R |
|---|---|
| Baldrinal | $COCH_3$ |
| Homobaldrinal | $COCH_2CH(CH_3)_2$ |

Genotoxicity has been reported for both baldrinal and homobaldrinal. The compounds showed direct mutagenic effects in vitro in the AMES assay and the SOS-chromo-test (von der Hude, et al. 1986). In addition, metabolic degradation of $^{14}$C-methacetin was distinctly inhibited in vivo by baldrinal (26 mg/kg) and homobaldrinal (31 mg/kg) administered either IP or PO to mice (Braun et al., Studies on the effects of Baldrinals on hemopoietic cells in vitro, 1986; 52: 446–450), indicating decreased liver function.

Accordingly, it is desirable to eliminate, or substantially reduce the level of, valepotriates and valepotriate decomposition products, such as baldrinals, in valerian extracts with respect to the levels of valepotriates in the root or biomass. The extraction method of the present invention achieves this objective, while simultaneously achieving the objective of extracting a measurable quantity of valerenic acid as described above.

Definitions

As used herein, the term "valerian" refers to any plant of the Valerianaceae family possessing extractable valerenic acid in its roots, and therefore refers, at least to, the plant designated *Valeriana officinalis* L. or alternatively herein, *V. officinalis* L. This species includes all recognized subspecies of *Valeriana officinalis* L. Some of these subspecies are also commonly referred to, in alternative taxonomic systems, as: *Valeriana exaltata* J. C. Mikan, *Valeriana nitida* Kreyer, *Valeriana palustris* Wibel, *Valeriana wolgenis* Kazak, *Valeriana grossheimii* Vorosch, *Valeriana collina* Wallr, *Valeriana Rossica* P. A. Smirn, *Valeriana spryngini* P.S. Smirn, *Valeriana angustifolia* Tausch, *Valeriana tenuifolia* Vahl, *Valeriana wallrothii* Kreyer, *Valeriana ucrainica* Demjan, *Valeriana sambucifolia* J. C. Mikan, *Valeriana excelsa* Poir, and *Valeriana officinalis* L.subsp. excelsa (Poir.) Rouy. Plants of the species *Valeriana officinalis* L. may be characterized as follows: These plant grows from a short rhizome to 2 m high, flowers, and then dies back again in the winter. These plant has pinnately-divided leaves with six to ten pairs of lance-shaped leaflets, and bears many small white or pink flowers in a dense head of several stalked clusters. These heads bare small (5 mm) tapered seeds.

As used herein, the term "valerian extracts" most generally refers to the composition isolated from the roots of plants of the Valerianaceae family according to a specified extraction procedure, and preferably refers to the composition isolated from the roots of valerian or *Valeriana officinalis* L. according to a specified extraction procedure. These extracts comprise essential oils, valerenic acids, valepotriates (iridoids), kessane derivatives, valeranone, valerenal, fatty acids, carbohydrates and certain amino acids.

As used herein, the term "valerenic acids" refers to all chemically stable derivatives of valerenic acid. In its most limited, and preferable, connotation, this term refers to valerenic acid, acetoxyvalerenic acid, and hydroxyvalerenic acid (these three compounds, in aggregate, are also referred to herein as "VAas"). These compounds, either individually, in the aggregate, or based on their respective ratios, may be used as standards to evaluate the extract processes herein described and/or to evaluate the plant from which the extracted roots have been obtained. Valerenic acid, in particular, may be used to verify that the roots extracted are of the species *Valeriana officinalis* L.

Valerenic acid (also referred to herein as "VA") is represented by the formula $C_{15}H_{22}O_2$, has a molecular weight of 234.33 amu, a UV $\lambda_{max}$ at 218 nm with a log $\epsilon$ of 4.232, and an $[\alpha]^{20}_D$ of $-117.8°$ (c=1.64, EtOH). Acetoxyvalerenic acid (also referred to herein as "AVA") is represented by the formula $C_{17}H_{24}O_4$, has a molecular weight of 292.35 amu, a UV $\lambda_{max}$ at 217 nm with a log $\epsilon$ of 4.184, and has an $[\alpha]^{20}_D$ of 36.7° (c=1.15, EtOH). Hydroxyvalerenic acid (also referred to herein as "HVA") is represented by the formula $C_{15}H_{22}O_3$, has a molecular weight of 250.34 amu, a UV $\lambda_{max}$ at 212 nm with a log $\epsilon$ of 4.305, and has an $[\alpha]^{20}_D$ of $-98.4°$ (c=0.63, EtOH). Accordingly, UV measurements at 220 nm may be used to determine the content of the valerenic acids in a given sample or aliquot.

As used herein, the term "valepotriates" (these compounds, in aggregate, are also referred to herein as "VPs") refers to all chemically unstable, thermolabile triesters of polyalcohols having an iridoid structure that may be found in the roots of members of the Valerianaceae family. The most typical valepotriates, as that term is used herein, are the diene-type valepotriates, valtrate, acevaltrate, and isovaltrate. The decomposition products of valepotriates, for example, baldrinal and homobaldrinal are not within the definition of "valepotriates," but may be referred to as "valeportriate derivatives" or "valepotriate decomposition products." UV measurements at 200, 254, and 320 nm are preferably used to determine the content of valepotriates in a given sample or aliquot.

As used herein, the term "volatile oils" refers to all oils in *V. officinalis* that are volatile, for example valerenal, valerenol, camphene, bornyl derivatives, myrtenyl acetate, and kessane derivatives.

As used herein, the term "isolated" refers to the state of being free of other, dissimilar compounds with which the extracted components of the invention will normally be associated in their natural state, so that upon being "isolated" the pharmaceutically-active components comprises at least about 0.25%, about 0.5%, about 1%, about 2%, about 4%, about 5%, about 10%, about 20%, about 50%, and at least about 75% of the mass, by weight, of a given sample.

As used herein, the term "water" refers to water, and preferably to potable water, which term includes purified and/or de-ionized water (DIW). Water, as used herein, may have dissolved within it a significant amount of any water-soluble solute, such as a salt or a sugar.

As used herein, the term "alcoholic" refers to a process of or an extract obtained from extraction in an alcoholic extraction solvent containing a significant percentage of alcohol. "Alcoholic extraction solvent" refers to extraction solvent having greater than approximately 10% alcohol by volume, and preferably refers to extraction solvents having at least approximately 25%, 30%, 35%, 40%, 45%, or preferably 50% alcohol by volume. Most preferably, "alcoholic extraction solvent" refers to an extraction solvent having alcohol content equal to or greater than approximately 70% by volume, and includes solvents that are 100% alcohol. Preferable, "alcoholic extraction solvent" refers to any $C_1$–$C_6$ alcohol, for example, methanol, ethanol, butanol or propanol, or any combination thereof, and most preferably refers to denatured ethanol (approximately 95% ethanol and approximately 5% methanol) The term "ethanol" should be understood as referring to denatured alcohol unless specifically identified otherwise.

As used herein, the term "roots" refers to all of subterranean portion of a specifically or generically identified plant, including, but not limited to, the roots, the rhizomes, and the stolons of the specifically or generically identified plant. Where the term "roots" is not modified by a specifically or generically identified plant, it will be understood that the term refers to the roots of the species, and subspecies of, *Valeriana officinalis* L.

Extraction Processes

The extraction processes provided herein most generally involve heating a mixture of the roots and an alcoholic extraction solvent for an extended period of time to obtain valerenic acid and valerenic acid derivatives in the extract, and to significantly reduce the amount of valepotriates in the extract. These processes, when compared to currently known processes, significantly reduce the amount of valepotriates in the valerian extract, while maximizing the amount of valerenic acid and of valerenic acid derivatives. It is contemplated that the extract, isolated according to the method of the present invention, may ultimately be used for a pharmaceutically active formulation.

The method includes an extraction process. An overall method for preparing such a pharmaceutically active formulation is described to place the extraction process in the context of the preparation of the pharmaceutically active formulation. The following five steps comprise a preferred method for preparing such a formulation: Pre-Extraction Processing of the Root, Extraction, Drying and Milling of the Drug Substance, and Formulation of a Tablet or Capsule. Additional or alternative steps, as well as the use of different pharmaceutical formulations, may be added without departing from this process.

Pre-Extract Processing of the Root

The roots may be prepared for extraction by grinding, chipping, or pulverizing to a powder in a hammermill, or like an instrument, as will be appreciated by those of skill in the art. After such pre-extraction processing, preferably at least 70%, 75%, or 80%, and most preferably 85% or 90% of the mass of the roots pass through a Tyler 20-mesh screen. Also preferably, the raw or processed roots are stored in a durable non-reactive, preferably plastic, and more preferably polyethylene, container or containers. These containers may be doubly-lined with bags of like material and closed or closeable with a lid composed of like material.

Extraction

The valerian root, whether, as preferred, processed as described above or in an unprocessed state, may be added to an extraction solvent. Most preferably, the root is added in a ratio of approximately one kilogram to approximately five liters of extraction solution. The extraction solvent preferably is an alcoholic extraction solution, comprising between approximately 30% to approximately 100% (volume/volume; v/v) alcohol and between approximately 70% (volume/volume; v/v) to 0% (v/v) water. Preferably, the alcoholic extraction solvent comprises approximately 50% to approximately 100% (v/v), approximately 55% to approximately 95% (v/v), approximately 65% to approximately 85% (v/v), and approximately 65% to approximately 75% (v/v) alcohol. Specifically, the alcoholic extraction solvent may comprise approximately 50% (v/v), approximately 60% (v/v), approximately 70% (v/v), approximately 80% (v/v), approximately 90% (v/v) alcohol and approximately 100% alcohol. The alcohol used in the alcoholic extraction solvent is fully miscible in water, and is preferably denatured ethanol (95% ethanol+5% methanol), but may be any $C_1$–$C_6$ alcohol, including but not limited to methanol, ethanol, n-butanol, isobutanol, n-propyl alcohol, and isopropyl alcohol.

The mixture of root and alcoholic extraction solvent may be stirred by any mechanical device conventionally known for such purpose, including but not limited to an overhead stirrer, a magnetic stirrer assembly, and/or a built-in stirrer, and may be suitable for or adapted to the particular extraction vessel employed. The mixture may be heated to between approximately 65° C. and 85° C., and more preferably between approximately 70° C. and 80° C., or alternatively, the temperature of reflux. Specifically, the mixture may be heated to 50°, 55°, 60°, 65°, 70°, 75°, 77°, or 80° or reflux. Various conventional methods may be used to heat the mixture, including but not limited to heating mantels or other resistive heating coils.

Preferably, the mixture is heated to any of the above-described temperature for at least one, one and one-half, two, two and one-half, three, three and one-half hours, four, or up to five hours. These durations, most preferably the latter three durations, are selected to significantly reduce the level of valepotriates relative to the initial value, preferably at least a 50% reduction. (Final Value/Initial Value=Percent Reduction). More preferably the reduction is by 60%, 70%, 75%, 80%, 90%, 95%, and most preferably 100% of the detectable level of valepotriates. In the latter case, the valepotriate level is not detectable by conventional techniques. The final valepotriate level may be obtained and may also be compared to that found in commercial valerian extracts.

Optionally, the mixture may then be cooled, preferably to room temperature or alternatively to a temperature above room temperature, including 30° C., 35° C., 40° C., 45° C., and 50° C. The solids may then be separated from the liquid (by filtration or centrifugation or any other conventional method for separation) . The extraction vessel and the separated solids may be rinsed with the extraction solvent, described above. For such a rinse, from approximately four liters, three liters, two liters, or preferably one liter of extraction solvent may be used for each kilogram of root initially extracted.

Also optionally, the filtrate containing the extracted material may be concentrated to an oily consistency under reduced pressure, including approximately 0.9, 0.8, 0.7, 0.6, and 0.5 atmospheres (atms), at a temperature above room temperature, including 30° C., 35° C., 40° C., 45° C., and 50° C. Optimally, a final volume of approximately 0.15 liters for each kilogram of root extracted is obtained.

Addition of Excipient to Facilitate Drying

The concentrate may be mixed with an excipient to facilitate drying. The excipient may be chosen from any commercially-available excipient or mixtures thereof, but is preferably selected from the following: maltodextrin-NF, tricalcium phosphate, silicon dioxide, dicalcium phosphate, microcrystalline cellulose, silicified microcrystalline cellulose, various ion exchange resins as will be understood by those of skill in the art, PVP/citrate, sodium citrate, pre-gelatinized corn starch (also known as Starch 1500), polyethylene glycol (PEG), sugar/polyol (also known as mannitol), TRIS buffer, sodium bicarbonate, porous silica, and combinations of the above-listed excipients and/or buffers, or other conventional excipient and any combination or mixture thereof as will be recognized by those of skill in the art. After addition of the excipient, the excipient will preferably comprise between approximately 10% and 40%, and more preferably between 20% and 25%, of the drug substance.

Drying and Milling of the Drug Substance

The concentrated valerian extract and excipient, if added, is dried under reduced pressure, including approximately 0.9, 0.8, 0.7, 0.6, and 0.5 atms, at a temperature slightly above room temperature, including 30°C., 35° C., 40° C., 45° C., and 50° C. Optimally, the drying is continuous until water content is equal to or less than less than 15%, 10%, or 5%, as measured by Karl Fischer analysis. The dried mixture may then be milled to a target of 80%, 85%, 90%, or 95% by weight passing through a size-exclusion screen of 60-mesh, 70-mesh, 80-mesh, 90-mesh, or 100-mesh.

Optionally drying of the extract may be accomplished by spray drying or any other conventional drying method as will be understood by one of ordinary skill in the art.

Certain of the constituents of *V. officinalis* L have been identified as sesquiterpenes (in the volatile oils) and iridoids (known as valepotriates). The total content of volatile oil varies widely within a single species, and also may vary between different species. The oil typically consists of mixtures of monoterpene and sesquiterpene derivatives. The amount of valepotriates also varies. The process of the present invention has been shown to reduce the amount of valepotriates when compared to currently practiced valerian extraction processes.

When verifying the plant source and process of the extraction process of the present invention, valerenic acid, acetoxyvalerenic acid, and hydroxyvalerenic acid are preferably used as marker compounds for analysis of the extract and later formulations based on the extracts. The process of the present invention significantly reduces the amount of valepotriates, while optimizing the yield of valerenic acid, acetoxyvalerenic acid, and hydroxyvalerenic acid either alone or in the aggregate. Active constituents of the extract of the present invention include, but are not limited to, valerenic acid and its derivatives (for example, acetoxyvalerenic acid and hydroxyvalerenic acid), kessane derivatives, valeranone, valerenal, small chain carboxylic acids, fatty acids and amino acids; the extract may also contains sugars and trace amounts of other aliphatic acids, alkaloids, phenolic acids, flavonoids, free fatty acids, sugars, and salts.

The present invention is herein described in detail through a variety of examples. It will be understood by those skilled in the art that the invention is not limited to the specific examples provided herein. Furthermore, although various amounts of plant material, specifically, *V. officinalis* L roots, and various other parameters under which extractions are performed, including specific pH conditions, temperatures, durations, and extraction solvents, are specified in the following examples, it will be understood by those skilled in the art that the invention is not limited to these specific plants, and these specific amounts and/or parameters. It will also be understood by those skilled in the art that the amount or type of plant material, the pH, temperature, solvent, and/or duration of extraction may be varied, and that the resultant process will still achieve one or more of the objectives of the invention.

EXAMPLE 1

Process for Valerian Root Extraction

The following process yielded dried valerian root extracts. The process also provided a free-flowing powder containing 0.3% to 0.8% valerenic acids and substantially reduced levels of valepotriates. Key process parameters were identified and acceptable ranges established. The process is as follows: chipped roots were extracted in 70:30 v/v denatured ethanol and potable water (EtOH/$H_2O$) maintained at approximately 70–75° C. for three hours; the filtrate was cooled to approximately 20–30° C. and the biomass was removed by filtration; the solvent was removed under vacuum at a temperature not greater than 40±5° C.; the residual oil was added to a maltodextrin excipient; and the product was dried and milled.

The process parameters and their respective effects were as follows:

Temperature. The reduction of valepotriates was temperature-dependent, and proceeded more rapidly at higher temperatures. After three hours at 70° C., reduction of the main valepotriate UV peak was approximately 90%; after three hours at reflux temperature (79–81° C.) the main valepotriate UV peak was reduced by over 99%. Recovery of valerenic acids was optimal at temperatures between 40° C. and 80° C.

Solvent composition. 70%:30% (v/v) EtOH/$H_2O$ was used as the extraction solvent. However at EtOH concentrations between 50% and 100%, statistically similar recoveries of valerenic acids were recorded.

Solvent volume. Similar amounts of valerenic acids were extracted when from four to seven volumes (one volume being 1 milliliter/1 gram of roots) of extraction solution were used. A volume of five times the mass of the roots was preferred.

Amount of Excipient. The minimum amount of excipient that yielded a friable product was approximately 20% with respect to the weight of the roots. The Following materials and reagents were used in this Example: chipped valerian roots; denatured ethanol (SDAG-1 grade from Commercial Alcohols, Inc. containing 95% ethanol and 5% methanol) RM0077; maltodextrin (Maltrin® M-040) NF grade from Grain Processing Corporation; extraction solution: seven volumes of denatured ethanol per three volumes of potable water; Reeve Angel 202 filter paper.

The following procedure was performed in this Example.

Ground roots (in three quantities: 250.0±0.1 g, 500.0±0.1 g or 1000±0.1 g) of the plant *V. officinalis* L (Aromatics, Inc., 460 Lancanster Dr., Salem, Oregon) were obtained. A 3-neck round bottom flash was placed in a water bath, or, alternatively, in or a heating mantle connected to a voltage regulator. A condenser and an overhead stirrer were connected to the flask. Using a graduated cylinder, five volumes of extraction solvent were measured, (with respect to the mass of the roots) using a 70% denatured ethanol: 30% potable water extraction solvent. The volumes were as recited in Table 2.

TABLE 2

| Volumetric Measurements of An Extraction Solvent For Various Roots Masses | |
|---|---|
| Weight of roots | Volume of 70% ethanol |
| 250 grams | 1250 milliliters |
| 500 grams | 2500 milliliters |
| 1000 grams | 5000 milliliters |

Root powder and 70%:30% v/v EtOH/$H_2O$ were added to the flask and the overhead stirrer was started. A 1.5 mL standard sample was removed and centrifuged. The temperature was continually monitored with a calibrated thermometer or thermocouple. When the temperature of the slurry reached 70–75° C., timing was started. 1.5 mL samples were removed at 30-minute intervals, and the temperature was maintained at approximately 70–75° C.

After 3 hours±15 minutes the slurry was cooled using external cold tap water to approximately 20–30° C. The slurry was filtered under vacuum (5 in. Hg) through Reeve Angel 202 filter paper. A 15 cm filter was used for the 250 gram sample, a 20 cm filter for the 500 gram sample and a 25 cm filter for the 1000 gram sample. These samples were washed using two volumes (with respect to the initial weight of the root powder) of 70%:30% v/v EtOH/H$_2$O. As the liquid left the surface of the filter cake, the cake wash was applied. After the cake wash was filtered, the cake was dried under full vacuum. Two 5.00 mL samples of filtrate were transferred into tared disposable aluminum dishes for determination of the nonvolatile residue content of the filtrate. The samples were dried on a hotplate using the lowest heat setting and the drying was completed under a vacuum for approximately 1–2 hours at approximately 40±5° C. The solvent was removed from the filtrate on a rotary evaporator connected to house vacuum. A bath temperature, initially at 25–30° C., was increased gradually to 40±5° C. The sample was concentrated until thick. Maltodextrin equal to 20% of the starting weight of the root powder was added, using a glass 10 mL pipette, while being rapidly stirred with a metal spatula until homogeneous. The maltodextrin root extract mixture was dried overnight in a drying oven using house vacuum at 40±5° C. The dried product was ground using a mortar and pestle.

EXAMPLE 2

Process for Valerian Root Extraction

Conditions identical to those detailed in Example 1 were used, except for the following: The temperature during the sample concentration was increased to 45±5° C. rather than to 40±5° C., and the sample was dried using a forced air drying oven with the temperature set at 40–50° C., rather than with a vacuum oven.

EXAMPLE 3

Process for Valerian Root Extraction

Conditions identical to those listed in Example 2 were created, except for the following: The flask used in the rotary evaporation step was rinsed thoroughly with 50 mL of extraction solution, and the rinse was concentrated in a 100 mL flask before it was added to the excipient.

EXAMPLE 4

Process for Valerian Root Extraction

Conditions identical to those listed in Example 1 were created, except for the following: One half of the filtrate was dried in two stages (I) 80% of the solvent was removed on a rotary evaporator at a vacuum of (16–25 mbar) and at a temperature of ≦35° C., and (ii) the remaining solvent was removed on trays in a forced-air drying oven at a temperature of ≦35° C. under atmospheric pressure; the concentrate was removed from the trays using an approximate equal weight of denatured ethanol; the ethanolconcentrate mixture was slurried with an amount of maltodextrin equivalent to 15% of the expected final powder weight; the spent biomass was re-extracted with 70% ethanol to determine whether a greater amount of valerenic acids is recovered under such conditions; lesser amounts of maltodextrin were used.

Also, a series of trials was carried out using 40%, 35%, 30% and 25% maltodextrin to determine the minimum amount required to produce a solid product after the sample was dried; and 1% silicon dioxide was included in several samples to determine whether it reduces the amount of maltodextrin required to produce a solid dried product.

EXAMPLE 5

Process for Valerian Extraction

Conditions identical to those listed in Example 1 were created, except for the following: The root-solvent mixture was refluxed for 3 hours (77–79° C.) rather at 70–75° C. as in the previous four demonstration runs; the amount of maltodextrin used was reduced by approximately two-thirds, i.e., 67 g rather than 200 g was used; the product was dried in a vacuum oven at 50° C. under a vacuum of 25–26 in. of mercury (Hg).

p Summary of the Results from Examples 1 through 5

Examples 1, 2, 3, 4, and 5 are meant to exemplify protocols and process parameters under which the objectives of the present invention may be achieved. Certain of the process parameters of Examples 1, 2, 3, 4, and 5 of the Valerian Root Extraction Processes are provided in Table 3.

TABLE 3

Demonstration Run Methods and Parameters

| Example # | Scale (g of roots) | Extraction Temp.(° C.) | Filtrate Concentration Method | Drying Method |
|---|---|---|---|---|
| 1 | 250 | 70-75 | Rotary evapor. (<40° C.) | Vac. oven at 40° C. |
| 2 | 250 | 70-75 | Rotary evapor. (<45° C.) | Forced air at 40–50° C. |
| 3 | 500 | 70-75 | Rotary evapor. (<45° C.) | Forced air at 50° C. |
| 4 | 1000 | 70-75 | Rotary evapor. (<35° C.) + Forced Air (35° C.) | Not dried |
| 5 | 1000 | 77-79 (Reflux) | Rotary evapor. (<50° C.) | Vac. oven at 50° C. |

*Only one-half of the filtrate was concentrated by this method

Effects of extraction temperature. As shown in Table 4, valepotriate levels decreased during the heating of the extraction mixtures. The reduction in valepotriate levels was much faster at reflux temperature (77–79° C.) than at 70–75° C. After three hours the valepotriate levels in Example 5 were 23%–30% of those in Example 1, 2, 3, and 4. The levels of valerenic acids were not affected by extraction temperature or time. They reached their maximum by the time the extracts attained the target temperatures and remained constant during the three hour heating period. Table 10 shows the average levels of total valerenic acids observed in the unfiltered extracts. The amounts appeared to be greater in Examples 1 and 2 than in Examples 3, 4, and 5. However differences may be attributed to differences in the standard curves employed for acetoxyvalerenic acid.

TABLE 4

Peak Areas (254 nm) for Valepotriates with Retention Time = 29 Minutes (5× dilutions)

| Time (hour) | Example 1 | Example 2 | Example 3 | Example 4 | Example 5 |
|---|---|---|---|---|---|
| 0 | 438,602 | 432,013 | 284,766 | 316,368 | 167,548 |
| 0.5 | 213,695 | 212,836 | 151,955 | 185,597 | 54,976 |
| 1.0 | 102,824 | 105,555 | 80,681 | 99,191 | 19,205 |
| 1.5 | 50,250 | 52,353 | 39,294 | 55,816 | 8,238 |
| 2.0 | 29,430 | 25,523 | 22,723 | 32,193 | 4,480 |
| 2.5 | 16,243 | 16,274 | 15,391 | 19,315 | 3,226 |
| 3.0 | 10,976 | 11,345 | 10,069 | 12,690 | 2,972 |

TABLE 5

Valerenic Acids Content in Unfiltered Extracts

| Example # | Scale (g of roots) | Average Concentration of VAs (µg/mL) | Total VAs in Extract (mg) | % roots' weight |
|---|---|---|---|---|
| 1 | 250 | 410 | 512 | 0.205 |
| 2 | 250 | 400 | 500 | 0.200 |
| 3 | 500 | 339* | 847 | 0.169 |
| 4 | 1000 | 361* | 1805 | 0.180 |
| 5 | 1000 | 359* | 1793 | 0.179 |

*New standard curves were utilized for these measurements.

Effects of temperature and vacuum on valerenic acid recovery. The low recovery of valerenic acids in Example 1 (see Tables 5 and 6) was initially attributed to their volatility and loss under the effects of vacuum and heat during the concentrating and drying steps. In subsequent Examples 2, 3, 4, and 5, changes were made in these steps as outlined in Table 3. For example, forced air drying rather than vacuum oven drying was used in Examples 2 and 3. Although the yields of valerenic acids improved slightly (Table 6), this improvement was attributed to better rinsing of the evaporator flask.

The effects of temperature and vacuum on valerenic acids recovery were investigated in a small-scale experiment carried out with aliquots of filtrate from Example 4. Samples of filtrate were dried under the conditions described in Table 3 and then reconstituted and analyzed for valerenic acids. The results indicated that there were no significant losses, even at 50° C. under vacuum for 72 hours, and that vacuum tray drying could be used without appreciable loss of valerenic acids. This result was confirmed in Example 5 where the product was dried at 50° C. under house vacuum and a valerenic acids recovery was 92% (Table 7). However, under these conditions the drying process was very slow, requiring 3.5 days. The two step concentrating procedure used in Example 4 was determined to be non-optimal due to the time required to complete the forced air drying and due to the difficulty of mixing the excipient with the residue.

TABLE 6

Final Powders Analyses

| Example # | Scale (g roots) | Powder Weight (g) | % VAs | Total VAs (mg) | % Recovery* |
|---|---|---|---|---|---|
| 1 | 250 | 95.7 | 0.346 | 331 | 65 |
| 2 | 250 | 94.7 | 0.446 | 423 | 85 |
| 3 | 500 | 191.3 | 0.388 | 742 | 88 |
| 4 | 1000 | Not appl. | Not appl. | Not appl. | Not appl. |
| 5 | 1000 | 267.0 | 0.616 | 1643 | 92 |

*expressed as a percentage of the valerenic acids content of the unfiltered extracts

TABLE 7

Valerenic Acids Recovery in Small-Scale Drying Experiments

| Drying Method | Valerenic Acids in Reconstituted Samples (µg/mL) |
|---|---|
| None (Filtrate) | 54.2 |
| Room temp., 25–26 in. vacuum, 72 h | 54.4 |
| 35–43° C., 1 atm, 72 h | 53.2 |
| 50° C., 25–26 in. vacuum, 72 h | 53.4 |
| 50° C., 25–26 in. vacuum + maltodextrin, 72 h | 53.7 |

Extracted solids. Table 8 provides a summary of the total dissolved solids (TDS) in the filtrates (determined using 5.00 mL samples) and the weight of solids (minus excipient) recovered in the final dried product. The extracted solids in the final product ranged from 17.9% to 20.0% of the weight of the roots.

TABLE 8

Extracted Solids

| Example # | Scale g of roots | TDS in Filtrate (% of root weight) | Final powder weight less weight of excipient (% of roots' weight) |
|---|---|---|---|
| 1 | 250 | 55.8 g (22.3%) | 45.7 g (18.3%) |
| 2 | 250 | 46.1 g (18.4%) | 44.7 g (17.9%) |
| 3 | 500 | 92.2 g (18.4%) | 91.3 g (18.3%) |
| 4 | 1000 | 199.5 g (20.0%) | Not Applicable |
| 5 | 1000 | 186.0 g (18.6%) | 200. g (20.0%) |

Amount of Excipient Added. In Examples 1, 2, and 3 the final product contained approximately 52% maltodextrin by weight. Small-scale trials using portions of the filtrate from Example 4 indicated that the amount of maltodextrin could be reduced to 25% of the final powder weight. In Example 5 the amount of maltodextrin was reduced accordingly and this resulted in a substantial increase in the weight percentage of valerenic acids in the final powder (Table 18).

From the above data, the following conclusions were drawn:

The optimum temperature for substantial reduction of valepotriate levels was reflux temperature (77–79° C.).

Losses of valerenic acids were not significant at 50° C. under vacuum.

The maltodextrin content may be reduced to 25% of the final powder weight.

EXAMPLE 6

Extraction in Water does not Yield Valerenic Acids

The method of Cerise et al. (U.S. Pat. No. 5,211,948) was used to attempt to extract valerenic acids from valerian root powder.

Valerian root powder was obtained from Triarco Industries, Lot LA019, lot size 25 kg. 10 g of valerian root powder was suspended in 60 mL of deionized water (DIW), and placed in a 70° C. bath and stirred with an overhead stirrer for 1 hour. The sample was then cooled in tap water to 20° C. 2.5 grams of Celite Hyflo Super Cel ("HyFlo") was added and the slurry filtered through a 5.5 cm filter pre-coated with 2.5 g Hyflo. Vacuum=5". Cake Wash=40 mL of DIW added after 3 min. Filtrate volume=85 mL. Color—very dark brown. Total filtrate time=2.5 min. The solid content of the filtrate was determined as follows: 1.00 mL of filtrate was added to an aluminum dish and evaporated to dryness on a hotplate. The dish was then dried for 1 hour in a vacuum oven at 70° C. under house vacuum. The disk was then cooled in a desiccator.

Water was evaporated from the bulk sample on a rotary evaporator at a temperature of approximately 50° C. The contents were emptied into a graduated cylinder, rinsed with de-ionized water (DIW) to a total volume of 24 mL. Twenty-four mL of 95% ethanol: 5% methanol was added. After 1 hour the sample was centrifuged, the supernateant was decanted, and the solid content was determined. The dried extract was dissolved in 20 mL of DIW and lyophilized overnight at 60° C. Drying was completed at 90° F. for 1 hour. The lyophilized samples were pulverized and analyzed by HPLC. There were no significant amounts of valerenic acid or acetoxyvalerenic acid present, as determined by HPLC or UV analysis.

The valerian root powder does not contain water-extractable valerenic acid, acetoxyvalerenic acid, or hydroxyvalerenic acid.

EXAMPLE 7

Extraction in Water does not Yield Valerenic Acids

The following procedure was used to determine the yield of valerenic acids from valerian root powder extracted at room temperature with a 50%/50% (v/v) mixture of alcohol and water, and to compare said extraction with a 100% water extraction.

In a first sample, ten grams of valerian root powder was stirred at room temperature with 30 mL of 95% ethanol:5% methanol plus 30 mL of deionized water for 2 hours with a magnetic stirrer. One mL of the suspension was centrifuged and a 250× dilution of the suspension was prepared in deionized water.

A second sample of powder root was prepared from the same lot in deionized water in the following manner: 200 mg of root powder was dissolved in 5 mL of deionized water. Absorbance spectra of the two samples were obtained and indicated different amounts of valerenic acid in the two samples. While the 50% ethanol extraction showed an absorbance maximum at 220 nm, the water extraction showed no absorbance maximum at 220 nm. The respective absolute intensities were 1.15 and 0.24.

This result confirms that the water based extract of the root of valerian does not contain valerenic acids.

EXAMPLE 8

Extraction in Water does not Yield Valerenic Acids

Between 200 and 250 mg of root powder were added to three separate 10 mL volumetric flasks. In the first flask, deionized water was added. To the second flask, an equal volume of 50% ethanol/50% water (v/v) was added. To the third flask, an equal volume of HPLC grade pure ethanol was added. Each flask was stirred at room temperature for 15 min and then filtered through 0.45 μm filters into HPLC vials. The resulting HPLC analysis led to the approximated results shown in Table 9.

TABLE 9

Results of Example 8

| Solvent | Total Valerenic Acids (Relative Intensity) |
|---|---|
| Pure water | 0.085 |
| 50% ethanol | 0.24 |
| Pure ethanol | 0.20 |

These results indicate that 100% water is not viable to use for extraction of valerenic acids. However, both 50% ethanol, and pure ethanol gave reasonably good results with respect to valerenic acids extraction.

EXAMPLE 9

Extraction in Water does not Yield Valerenic Acids—Comparison Between a Prior Art Extraction Method and a Method of Current Invention The process described in the U.S. Pat. No. 5,211,948 was duplicated and the precise amounts of the three previously described valerenic acids were quantitated by liquid chromatography. First, 25 mg of finely powdered roots of *V. officinalis* was extracted with 150 mL of water heated to an average temperature of 70° C. for a period of 4 hrs. The water extract was separated from the ground root and concentrated at 50° C. under vacuum to a dry matter content of about 14%. To this concentrate an equal volume of ethanol was added to attain a final concentration of 50% ethanol. After standing for a period of 8 to 20 hr at room temperature, the precipitate formed was removed. The above-described extraction process was repeated two more times with 100 mL of fresh water each time and heated for 3 and 2 hr, respectively. Each extract was analyzed for total valerenic acids using an HPLC method and the results are summarized in Table 15.

To determine whether the valerenic acids remained behind with the valerian root, the "spent" valerian root biomass was extracted subsequently with 330 mL of denatured ethanol (about 70% ethanol, final concentration) for 10 to 15 min. The ethanolic extract was analyzed for valerenic acids and the results, shown in last row of Table 10.

The process described in the current invention was duplicated and the amounts of total valerenic acids were quantitated by liquid chromatography, as follows: 25 gm of finely powdered roots of *V. officinalis* was extracted with 125 mL of 70% denatured ethanol by refluxing at 70° C. for a period of 5 hr. The hydroalcoholic extract was separated from the biomass and analyzed for total valerenic acids by an HPLC method. The results are summarized in Table 11.

TABLE 10

Extraction of Three Valerenic Acids - Prior Art Process

| Sample Description | Hydroxy-valerenic acid (mg) | Acetoxy-valerenic acid (mg) | Valerenic acid (mg) | Total Valerenic acids* (mg) |
|---|---|---|---|---|
| Extract #1 | 0.144 | 0.575 | 0.366 | 1.085 |
| Extract #2 | 0.421 | 1.36 | 0.59 | 2.371 |
| Extract #3 | 0.407 | 1.2 | 0.338 | 1.945 |

TABLE 10-continued

Extraction of Three Valerenic Acids - Prior Art Process

| Sample Description | Hydroxy-valerenic acid (mg) | Acetoxy-valerenic acid (mg) | Valerenic acid (mg) | Total Valerenic acids* (mg) |
|---|---|---|---|---|
| Total from Extractions | 0.972 | 3.135 | 1.294 | 5.401 |
| Total Remaining in Spent Biomass** | 1.71 | 17.68 | 21.04 | 40.43 |

*Sum of Hydroxy-, acetoxy- and valerenic acids
**Valerenic acids extracted from spent biomass with 70% ethanol

TABLE 11

Extraction of Three Valerenic Acids

| Sample Description | Hydroxy-valerenic acid (mg) | Acetoxy-valerenic acid (mg) | Valerenic acid (mg) | Total Valerenic acids (mg) |
|---|---|---|---|---|
| Present Method | 1.34 | 25.43 | 23.79 | 50.56 |

The results of this example (see Table 10 and 11) demonstrate that total valerenic acids (hydroxyvalerenic, acetoxyvalerenic and valerenic acid) of *V. officinalis* root are poorly extracted by the process described by the U.S. Pat. No. 5,211,948, and that most of the acids remain behind in the spent biomass. Based on these results, it is concluded that valerenic acids are poorly soluble in water. Thus, the process described in the prior art patent does not effectively extract the valerenic acids from *V. officinalis* root.

In contrast, the process of the present invention, as shown in Table 11, is very efficient in extraction of total valerenic acids. A comparison of the extraction efficiency by these two processes, as summarized in Table 12, shows that the prior art process is only about 11% as efficient as the current process in extracting valerenic acids.

TABLE 12

Recovery Of Valerenic Acids-Prior Art Process vs. Method Presented Herein

| Sample Description | Hydroxy-valerenic acid (mg) | Acetoxy-valerenic acid (mg) | Valerenic acid (mg) | Total Valerenic acids (mg) |
|---|---|---|---|---|
| Present Invention | 1.34 | 25.43 | 23.8 | 50.6 |
| Prior Art Process | 0.97 | 3.13 | 1.3 | 5.4 |
| Isolation Efficiency* (%) | 72.5 | 12.3 | 5.4 | 10.7 |

*Efficiency of Prior art process as compared to Present Invention

EXAMPLE 10

Analysis of Volatile Oils in Valerian Samples Produced by a Prior Art Process and the Current Process Samples obtained using the process of the U.S. Pat. No. 5,211,948 and the current process (see Table 10 and 11 for sample description) were analyzed for the presence of volatile oils. Qualitative analysis of volatile oils was done on a Finnigan Trace GCMS instrument using a Supelco SPB-5 30 m×0.25 mm×0.25 µm column (length, diameter, packing thickness) maintained at a temperature of 280° C. Eluting peaks were monitored as positively charged mass units.

The chromatograms obtained according to the '948 patent clearly show that extraction of valerian root three times with hot water, does not yield any volatile oil peaks (the peak eluting around 40 min corresponds to siloxane, which is used as column coating). In contrast, the current process yielded numerous volatile oil peaks. To show that volatile oils are not destroyed by the '948 process but still remain with the biomass, the spent biomass was extracted with 70% ethanol. Numerous volatile oil peaks were observed in the chromatograms of the spent biomass, clearly indicating that the '948 process is unable to extract the highly polar volatile oils from the valerian roots The volatile oil component of *V. officinalis* makes a major contribution towards the sedative activity of valerian extract (Houghton 1997). Thus, the current process will yield a product rich in volatile oil and thus would be superior to the product obtained by the process of U.S. Pat. No. 5,211,948.

EXAMPLE 11

Two lots of *V. officinalis* root were analyzed for Valepotriate content as follows. At the time of analysis, approximately 18 months to approximately 6 months had passed from the date of harvesting. Valtrate and isovaltrate were measured in each biomass sample utilizing an HPLC method coupled to a diode-array detector, while didrovaltrate (which is present in trace amounts) was analyzed using a more sensitive LC/MS/MS method. Reference standards, made at Ancile Pharmaceuticals, Inc., San Diego, Calif., for each of these valepotriates were used, and Standard HPLC and LC/MS/MS methods were employed as follows : The valepotriates isovaltrate and valtrate were analyzed by an HPLC method using a C-18 reverse phase column (4.6×250 mm, 4 µm particle size) Valepotriates were monitored at their UV absorbance maximum of 254 nm. The retention time of isovaltrate and valtrate under the LC conditions were about 28.9 and 30.1 min, respectively. Didrovaltrate was analyzed by a LC/MS method using a C-18 (3×150 mm, 3 µm particle size) column. Didrovaltrate was detected by Selective Ion Monitoring in MS2 positive ion mode. Retention time under the LC condition was about 8.0 min.

Valepotriate peaks were identified based on their relative elution times as compared to the standards as well as their characteristic UV absorption spectrum. See Bos R. et al., Analytical aspects of Phytotherapeutic Valerian preparation, 1996; 7:143–151) and/or molecular mass. The quantitative results are summarized in Table 13. Valtrate and isovaltrate were shown to be present in low amount (<0.5%), whereas the monoene valepotriate, didrovaltrate, was present in trace quantities (<0.005%). In addition, analysis of the extract, revealed that following the extraction process, the content of didrovaltrate is below the limit of detection (<7 ppm) of LC/MS/MS methods.

TABLE 13

Valepotriate Content in *V. officinalis* Dried Roots

| | Content in dried root (% w/w) | | |
|---|---|---|---|
| *V. officinalis* | Isovaltrate | Valtrate | Didrovaltrate |
| Sample 1 | 0.40 | 0.049 | 0.0045 |
| Sample 2 | 0.19 | 0.045 | 0.0022 |

EXAMPLE 12

As described earlier, the present extraction process significantly reduces the levels of valepotriates in the extract with respect to the content in *V. officinalis* biomass. To demonstrate that this process does not result in the accumulation of potentially toxic baldrinals, the extract was analyzed for its baldrinal and homobaldrinal content.

Homobaldrinal is present in an extract according to the invention at only 5.9 ppm, and the level of baldrinal is below the limit of detection of the assay (<3 ppm). Similar results were obtained for the content of isovaltrate and valtrate in this extract. In contrast, the starting biomass contained 4000 ppm isovaltrate and 490 ppm valtrate. This data, summarized in Table 14, demonstrates that the current extraction process significantly reduces valepotriate levels but does not result in the accumulation of baldrinals. The levels of homobaldrinal and baldrinal may be collected to confirm, across manufacturing runs, that the baldrinals are not produced during the extraction processes.

TABLE 14

Levels of Valepotriates and their Degradation Products in the Current Extract

| Compound | Level in the Extract (ppm) | |
| --- | --- | --- |
| | The Starting Biomass | The Extract |
| Valtrate | 490 | ND |
| Isovaltrate | 4000 | <24 |
| Baldrinal | NT | ND |
| Homobaldrinal | NT | 5.9 |

ND: Not detected
NT: Not tested

EXAMPLE 13

Temperature and Volume Dependence of Extraction (30–50° C.)

This Example was conducted (1) to determine the amount of valerenic acids extracted from chipped valerian root at 30° C., 40° C. and 50° C.; (2) to determine the effect of using a large volume of extraction solvent; (3) to determine—if homogenizing the mixture releases valerenic acids more efficiently than stirring; (4) to determine if using absolute ethanol rather than 95% ethanol:5% methanol effects the extraction process; (5) to evaluate percolation of the extraction; and (6) to determine if heating an extract at 42° C. efficiently destroys valepotriates.

The same materials as used in Examples 1–5 are used in this Example.

Ten grams of chipped root was stirred with 60 mL of extraction solvent using an overhead stirrer. 70% ethanol was used as the extraction solvent. Separate samples were prepared and stirred in the calibrated water bath for 1 hour. Temperatures of 30° C., 40° C. and 50° C. were used. Samples were covered with parafilm to prevent solvent evaporation. After 1 hour, samples were cooled to room temperature under cold tap water. Samples were filtered through 5.5 cm filters and the filter cake rinsed with 30 mL of the alcoholic extraction solvent. The solid content was determined by evaporating 3 mL aliquots on aluminum dishes using a hotplate and then drying in a vacuum oven at 55° C. for 1.5 h. Before HPLC analysis, a portion of each filtrate was diluted 10× with 70% ethanol and filtered through a 0.2 micron syringe filter. Portions were also diluted 50× in deionized water and UV/VIS spectra were obtained.

The samples, designated A, B, C, D, E, F, G, were differentiated as follows: Sample A was extracted at 30° C., Sample B was extracted at 40° C., Sample C was extracted at 50° C., Sample D was extracted in 90 mL of extraction solvent at room temperature, Sample E was extracted at room temperature, Sample F was extracted in absolute ethanol, and Sample G was extracted at 43° C. for two days. Results are shown in Table 15 and 16.

TABLE 15

Extracted Solids

| Sample | Volume (mL) | Weight % | $A_{275}$nm | $A_{320}$nm |
| --- | --- | --- | --- | --- |
| A | 75 | 16.6 | 1.055 | 0.724 |
| B | 71 | 17.5 | 1.301 | 0.433 |
| C | 68.5 | 17.0 | 1.361 | 0.432 |
| D | 107.5 | 18.8 | 0.886 | 0.545 |
| E | 78 | 13.2 | 1.220 | 0.803 |

TABLE 16

HPLC Results of This Example

| Sample | HVA | AVA | VA | Total VAs | VP ht/ VA ht** |
| --- | --- | --- | --- | --- | --- |
| A (30° C.) | 1.84 | 123 | 94.4 | 218 | 0.66 |
| μg/mL | | | | | |
| mg | 0.15 | 9.22 | 7.08 | 16.4 | |
| weight % | 0.002 | 0.092 | 0.071 | 0.164 | |
| B (40° C.) | 2.90 | 145 | 122 | 282 | 0.61 |
| μg/mL | | | | | |
| mg | 0.28 | 11.1 | 8.66 | 200 | |
| weight % | 0.0003 | 0.111 | 0.087 | 0.200 | |
| C (50° C.) | 3.78 | 161 | 123 | 238 | 0.51 |
| μg/mL | | | | | |
| mg | 0.26 | 11.0 | 8.4 | 19.7 | |
| weight % | 0.003 | 0.110 | 0.084 | 0.197 | |
| D (Room Temp.) | 1.74 | 97.9 | 77.6 | 177 | 0.69 |
| μg/mL | | | | | |
| mg | 0.187 | 10.5 | 8.34 | 19.0 | |
| weight % | 0.002 | 0.105 | 0.083 | 0.190 | |
| E (Room Temp.) | 2.14 | 137 | 105 | 244 | 0.69 |
| μg/mL | | | | | |
| mg | 0.17 | 10.7 | 8.2 | 19.1 | |
| weight % | 0.002% | 0.107% | 0.072% | 0.191% | |
| F (EtOH) | 2.14 | 182 | 139 | 232 | 0.64 |
| μg/mL | | | | | |
| mg | 0.013 | 1.09 | 0.83 | 1.93 | |
| weight % | 0.001% | 0.109% | 0.033% | 0.193% | |
| G (43° C.) | 2.48 | 117 | 96.4 | 216 | 0.13 |
| μg/mL | | | | | |
| mg | 0.186 | 8.78 | 7.23 | 16.2 | |
| weight % | 0.002% | 0.088% | 0.072% | 0.162% | |

**Ratio of Valepotriate peak at 29 minutes to Valerenic acid peak.

From this Example, it was determined that the optimum temperature for extracting valerenic acids is 40–50° C. The use of larger volumes of extraction solvent extracted about 15% more valerenic acids, and valerenic acids are stable in solution at 42° C. for 2 days, while valepotriates are not.

EXAMPLE 14

Temperature Dependence of Extraction (60° C.)

This Example was conducted to evaluate an extraction at 60° C. and to determine if similar amounts of valerenic acids and valepotriates are extracted as compared to extraction at lower temperatures.

Materials as used in Examples 1, 2, 3, 4, and 5 are also used in this Example.

The extraction of 15 g of ground roots with 75 mL of 70% ethanol was carried out in a 250 mL glass three-necked flask, equipped with a condenser and overhead stirrer. After 1 hour at 60° C., the sample was cooled and filtered through a 5.5 cm filter. 30 mL of cake wash was used. A 5× dilution was used for HPLC analysis. The dry weight was determined by evaporating 3 mL of filtrate in an aluminum pan on a hotplate and then placing the pan in a vacuum oven at 55° C. for 1 hour.

The results are shown in the Table 17.

TABLE 17

Results of Example 14.

|  | HVA | AVA | VA | Total | VP ht/ VA ht** |
|---|---|---|---|---|---|
| µg/mL | 3.661 g | 181.2 | 150.0 | 335 | 0.51 |
| total | 0.329 | 16.3 | 13.5 | 30.1 |  |
| weight % | 0.002 | 0.109 | 0.090 | 0.201 |  |

**Ratio of Valepotriate peak at 29 minutes to Valerenic acid peak.

From the data obtained in this Example, it was determine that, (i) at 60° C., the same amount of valerenic acids was extracted (approximately 0.2%) as at 40° C., but more solids were extracted at the higher temperature, (ii) significantly less valepotriates were extracted at 60° C., (previous peak ratios were 0.60–0.65), suggesting that longer extraction times and/or higher temperatures were effective in eliminating valepotriates.

EXAMPLE 15

Temperature Dependence of Extraction (80° C.)

In this Example, six samples of 100 grams of chipped roots were added to six aliquots of 500 mL of 70% ethanol, and were stirred at 80° C. for the following times: zero, one, two, two and one-half, three, and three and one-half hours. For each of these samples, an absorbance at 220 nm and 200 nm was observed to determine if the valerenic acid and acetoxyvalerenic acid concentrations varied. The valerenic acid and acetoxyvalerenic acid concentrations did not vary.

Furthermore, the concentration of valepotriates was determined for the two and one-half, three, and three and one-half hours samples. It was determined that there was no significant difference in percent reduction of valepotriates between two and one-half, three and three and one-half hours. Accordingly, it was determined that extraction times ranging from approximately two and one-half, to three and one-half hours could be employed at an extraction temperature of 80° C.

EXAMPLE 16 pH Dependence of Extraction

This Example was conducted to evaluate the effects of acidic pH and/or 70° C. temperature on valepotriate content, and more specifically to evaluate whether the valepotriates in root extracts could be removed by heating the extracts at 70° C. and maintaining the pH at 2–3.

Fifteen grams of ground root was added to 25 mL of 75% ethanol at room temperature, and the pH was adjusted to 2.2 with 1 N HCl. The following experiments were conducted:

Experiment A: fifteen grams of ground root was added to 75 mL of 70% ethanol at room temperature, and the pH adjusted 2.2 with 1 N HCl. Samples were removed to Time=1 hour and Time=2 hours, centrifuge, and the supernates were diluted 5× for HPLC analysis. The pH drifted upwards after 1 hour. Additional acid was added; a total of 7 mL was added. After 2 hours, the pH was adjusted to pH 6 with 1 N NaOH. Again, the pH drifted (downward) and was monitored and adjusted every 15 minutes.

Experiment B: Fifteen grams ground root was added to 75 mL of 70% ethanol, and was warmed to 70° C. in water bath. A 3-neck 250 mL flask plus condenser and overhead stirrer. Samples were taken at time=0, 1, and 2 hours then centrifuged and diluted as in Experiment A.

Experiment C: Identical to Experiment 1, except 7 mL 1 N HCl was added at time=0 and the pH was checked with pH paper to ensure that it was between pH=2 and 3; and rechecked after 1 hour. Samples were removed at time=0, 1, and 2 hours. The pH was adjusted to 6 with NaOH after 2 hours.

Experiment D: the sample obtained from Experiment 2 was rinsed with 30 mL cake wash; the pH of the filtrate was adjusted to 2.3 with 1 N HCl. The sample was stirred for 1 hour. The results of Experiments A, B, C, and D are shown in Table 18.

TABLE 18 pH Dependence of Extraction

| Time (hour) | VA (µg/mL) | VA. peak area at 220 nm | VP peak area at 220 nm (29 min peak) | Ratio of VP/VA** |
|---|---|---|---|---|
| Experiment A |  |  |  |  |
| 0 | 28.7 × 5 | 162,404 | 79,342 | 0.49 |
| 1 | 31.0 × 5 | 175,229 | 92,607 | 0.53 |
| 2 | 32.3 × 5 | 183,157 | 86,761 | 0.47 |
| pH readjust. | 35.0 × 5* | 198,278* | 135,803* |  |
| Experiment B |  |  |  |  |
| 0 | 34.8 × 5 | 196,699 | 80,889 |  |
| 1 | 35.8 × 5 | 202,532 | 43,476 |  |
| 2 | 39.1 × 5 | 221,412 | 11,388 |  |
| Experiment C |  |  |  |  |
| 0 | 31.6 × 5 | 178,843 | 63,650 |  |
| 1 | 33.4 × 5 | 188,808 | 21,815 |  |
| 2 | 32.9 × 5 | 185,843 | 13,618 |  |
| pH readjusted | 31.0 × 5 | 175,258 | 12,852 |  |
| Experiment D |  |  |  |  |
| 0 | 25.4 | 143,977 | 11,631 (5810) |  |
| 1 h | 26.1 | 147,925 | 12,955 (7233) |  |

**Ratio of Valepotriate peak at 29 min to Valerenic acid peak.

the data obtained in this Example, it was determined that, at room temperature, adjusting the pH to 2–3 had a small but immediate effect on the valepotriate peak with a retention time of 29 minutes. Specifically, this peak has an area that is typically approximately 60–65% of that of the valerenic acid peak at 220 nm. However, at pH=2–3, the peak area was 50% of the valerenic acid peak area. The reduction in area was the same at extraction times of two hours and zero hours. Also heating the extract at 70° C. destroyed the valepotriate peak. Each hour saw the peak area reduced substantially. At pH 2–3 and 70° C., the valepotriate destruction occurred substantially faster during the first hour. Notwithstanding the results of this Examples, the extract process may be performed at pH greater than about 3.0, greater than about 5.0, or greater than about 7.0.

EXAMPLE 17

Effect of Reflux and the Duration of Reflux on Extract

This Example was conducted to determine whether the content of valerenic acids, of valepotriates, and of extracted solids are effected after refluxing ground valerian root for 3 hours in 70% ethanol.

One hundred grams of ground root was added to 500 mL of 70% ethanol, transferred to a one liter, 3 neck flask equipped with a condenser and an overhead stirrer, and heated in a water bath. Samples were removed at time=zero, one, two and three hours respectively. Samples A, B, C, and D. After 3 hours the slurry was filtered on a 15 cm filter (RA202) and the filter cake was washed with 2 mL of 70% ethanol. Three 5 mL samples of filtrate were dried in aluminum dishes to calculate extraction efficiency. The rest of the filtrate was concentrated in a roto-evaporator.

The obtained samples were centrifuged. A portion of the supernatant was diluted 100× in extraction solvent and a UV/VIS spectrum was obtained. The remaining filtrate was mixed with 20 grams of maltodextrin and dried at 35° C., at reduced pressure, overnight.

The results are shown in Table 19, 20, 21 and 22.

TABLE 19

Extracted solids

| Sample | Tare Weight | Gross Weight | Net Weight | Average |
|---|---|---|---|---|
| A | 1.8822 g | 2.0365 | 0.1543 | |
| B | 1.8613 g | 2.0151 | 0.1538 | 0.1540 |
| C | 1.8721 g | 2.0260 | 0.1539 | |

TABLE 20

Valerenic Acids: (weight %)

| Sample | Time | HVA | AVA | VA | Total |
|---|---|---|---|---|---|
| A | 0 | 0.0023 | 0.099 | 0.075 | 0.176 |
| B | 1 h | 0.0036 | 0.122 | 0.092 | 0.213 |
| C | 2 h | 0.0041 | 0.121 | 0.095 | 0.226 |
| D | 3 h | 0.0055 | 0.125 | 0.099 | 0.230 |

TABLE 21

| Sample | $Abs_{275\,nm}$ | $Abs_{320\,nm}$ | $Abs_{400\,nm}$ | $Abs_{600\,nm}$ |
|---|---|---|---|---|
| A | 0.64786 | 0.52651 | 8.2934e-2 | 1.6159E-2 |
| B | 0.83918 | 0.74047 | 0.12043 | 3.4679E-2 |
| C | 0.83128 | 0.74164 | 0.10537 | 2.1706E-2 |
| D | 0.82511 | 0.73693 | 0.10685 | 2.9453E-2 |

TABLE 22

Retained Valepotriates

| Sample | UV Peak Area |
|---|---|
| A | 239,953 |
| B | 20,245 |
| C | 6,484 |
| D | 4,156 |

Table 23 shows data used on the refluxed root powder in this Example. The data in Table 23 were used as a standard.

TABLE 23

Data Used On The Refluxed Root Powder

| Sample | | HVA | AVA. | VA. | Total |
|---|---|---|---|---|---|
| #1 200 mg/10 mL | µg/mL | 2.39 | 39.47 | 29.60 | 71.96 |
| | wt % | 0.12 | 0.200 | 0.148 | 0.360 |
| #2 220.9 mg/103 mL | µg/mL | 1.14 | 43.7 | 33.2 | 72.04 |
| | wt % | 0.005 | 0.198 | 0.150 | 0.353 |
| | Avg. wt. % | 0.008 | 0.144 | 0.149 | 0.356 |

From the data obtained in this Example, it was determined that refluxing was an effective way to remove valepotriates. However, the yield of valerenic acids in the dry powder obtained from reflux was significantly lower than when the extraction was carried out at 70° C.

EXAMPLE 18

Effect of Heating Duration on Extract Valepotriate Content

In this Example, the extraction mixture was heated at reflux for three and one-half hours. This Example was conducted to determine if there are significant differences in the levels of valepotriates between three and one-half hours of reflux and the durations exemplified in the previous example.

TABLE 24

| | | µg/mL (× 5) | | | Valepotriate $R_t$ = 29.5 nm |
|---|---|---|---|---|---|
| Lot | Time (h) | HVA | AVA | VA | Peak area at 253 nm |
| RK27A | 2.5 | 0.06 | 40.2 | 31.2 | 3652 |
| RK27B | 3.0 | 0.9 | 40.1 | 31.3 | 2937 |
| RK27C | 3.5 | 0.9 | 40.4 | 33.3 | 3066 |

Total VA = 74.6 × 5 × .500 mL = 186 mg
Final Powder

TABLE 25

| Sample wt. | % HVA | % AVA | % VA | Total VAs |
|---|---|---|---|---|
| 227.4 | 0.004 | 0.135 | 0.107 | 0.246 |
| 218.0 | 0.0004 | 0.137 | 0.107 | 0.245 |

Total val. acids = 0.246 / 100 × 35.42 g = 87 mg (46.3%) valerenic acid peak at 254 nm.

From the data obtained in this Example, it was determined that there was little change in valerenic acid and valepotriate content in the extract when comparing reflux for three and three and one-half hours and the durations exemplified in the previous example.

The various articles of the scientific and/or medical literature, and the U.S. and international and/or foreign patents and patent applications cited herein are hereby incorporated by reference to the extent permitted by law. To the extent that each is incorporated by reference herein, each constitutes a part of the disclosure of this specification. Furthermore, specific embodiments, working examples, and prophetic examples of the invention have been described in detail to illustrate the broad applicability and principles underlying the invention. Notwithstanding these specific embodiments, working examples, and prophetic examples, it will be understood by those of skill in the art that the invention may be embodied otherwise without departing from such broad applicability and principles.

What is claimed is:

1. A process for preparing a pharmaceutically-active extract of the root of *Valeriana officinalis* L. comprising the steps of:

adding the roots to an alcoholic extraction solvent to form a mixture, wherein the alcoholic extraction solvent comprises between approximately 50% (v/v) to approximately 100% (v/v) ethanol in a remainder of water, and heating the mixture to a temperature of between approximately 70° C. to approximately 80° C. for a period of at least two hours;

wherein valerenic acid is present in the extract, the content of valepotriates and aldehyde-containing valepotriate decomposition products in the extract is substantially reduced with respect to the content of valepotriates in the root, and the content of valerenic acids in the extract is not substantially reduced with respect to the content of valerenic acids in the root; and wherein the pH of the mixture is maintained above approximately 5.0.

2. The process of claim 1, wherein the content of volatile oils in the extract is not substantially reduced with respect to the content of volatile oils in the root.

3. The process of claim 1, wherein the extraction solvent comprises between approximately 60% to approximately 80% ethanol.

4. The process of claim 1, wherein the extraction solvent comprises between approximately 65% to approximately 75% ethanol.

5. The process of claim 1, wherein the extraction solvent comprises approximately 70% ethanol.

6. The process of claim 1, wherein the mixture is heated to reflux.

7. The process of claim 1, wherein the mixture is heated for a period of at least approximately three hours.

8. The process of claim 1, wherein the mixture is heated for a period of at least approximately two hours.

9. The process of claim 5, wherein the mixture is heated for a period of at least approximately three hours.

10. The process of claim 1, including the additional steps of:

cooling the heated mixture, filtering remaining solids from the mixture, and rinsing the solids with the alcoholic extraction solvent.

11. The process of claim 10, wherein the heated mixture is cooled to between approximately 40° C. and approximately 50° C.

12. The process of claim 10, wherein the rinsing step comprises the use of approximately two liters of alcoholic extraction solvent for every kilogram of root.

13. A pharmaceutically-active extract of the root of a plant of the family Valerianaceae, obtained by a process comprising the steps of:

adding the roots to an alcoholic extraction solvent to form a mixture, wherein the alcoholic extraction solvent comprises between approximately 50% (v/v) to approximately 100% (v/v) ethanol in remainder of water, and heating the mixture to a temperature of between approximately 70° C. to approximately 80° C. for a period of at least two hours;

wherein significant amounts of valerenic acid and volatile oils are present in the extract; and wherein the pH of the mixture is maintained above approximately 5.0.

14. The process of claim 1, wherein the content of valepotriates in the extract is not detectable by conventional techniques.

15. The extract of claim 13, wherein the plant is *Valeriana officinalis* L.

16. The extract of claim 13, wherein the extraction solvent comprises approximately 70% ethanol.

17. The extract of claim 13, wherein the mixture is heated to reflux.

18. The extract of claim 13, wherein the mixture is heated for a period of at least three hours.

19. An ingestible entity comprising an extract isolated according to the method of claim 1.

20. An ingestible entity comprising the extract of claim 13.

21. The process of claim 6, wherein the mixture is heated to reflux for a period of at least approximately two hours.

22. A process for preparing a pharmaceutically-active extract of the root of *Valeriana officinalis* L. comprising the steps of:

adding the roots to an alcoholic extraction solvent to form a mixture, wherein the extraction solvent comprises between approximately 60% to approximately 80% ethanol in a remainder of water, and heating the mixture to a temperature of between approximately 70° C. to approximately 80° C. for a period of at least two hours;

wherein valerenic acid is present in the extract, the content of valepotriates and aldehyde-containing valepotriate decomposition products in the extract is substantially reduced with respect to the content of valepotriates in the root, and the content of valerenic acids in the extract is not substantially reduced with respect to the content of valerenic acids in the root; and wherein the pH of the mixture is maintained above approximately 3.0.

23. The process of claim 22, wherein the content of valepotriates in the extract is not detectable by conventional techniques.

24. An ingestible entity comprising an extract isolated according to the method of claim 22.

25. The process of claim 22, wherein the content of volatile oils in the extract is not substantially reduced with respect to the content of volatile oils in the root.

26. The process of claim 22, wherein the extraction solvent comprises between approximately 65% to approximately 75% ethanol.

27. The process of claim 22, wherein the extraction solvent comprises approximately 70% ethanol.

28. The process of claim 22, wherein the mixture is heated to reflux.

29. The process of claim 22, wherein the mixture is heated for a period of at least approximately three hours.

30. The process of claim 22, wherein the pH of the mixture is maintained above approximately 5.0.

31. The process of claim 27, wherein the mixture is heated for a period of at least approximately three hours.

32. The process of claim 22, including the additional steps of:

cooling the heated mixture, filtering remaining solids from the mixture, and rinsing the solids with the alcoholic extraction solvent.

33. The process of claim 32, wherein the heated mixture is cooled to between approximately 40° C. and approximately 50° C.

34. The process of claim 32, wherein the rinsing step comprises the use of approximately two liters of alcoholic extraction solvent for every kilogram of root.

35. The process of claim 22, wherein the mixture is heated for a period of at least approximately two hours.

36. The process of claim 28, wherein the mixture is heated to reflux for a period of at least approximately two hours.

37. A pharmaceutically-active extract of the root of a plant of the family Valerianaceae, obtained by a process comprising the steps of:

adding the roots to an alcoholic extraction solvent to form a mixture, wherein the extraction solvent comprises between approximately 60% to approximately 80% ethanol in a remainder of water, and heating the mixture to a temperature of between approximately 70° C. to approximately 80° C. for a period of at least two hours;

wherein significant amounts of valerenic acid and volatile oils are present in the extract; and wherein the pH of the mixture is maintained above approximately 3.0.

38. The extract of claim 37, wherein the plant is *Valeriana officinalis* L.

39. The extract of claim 37, wherein the extraction solvent comprises approximately 70% ethanol.

40. The extract of claim 37, wherein the mixture is heated to reflux.

41. The extract of claim 37, wherein the mixture is heated for a period of at least three hours.

42. An ingestible entity comprising the extract of claim 37.

* * * * *